United States Patent
Miyazaki et al.

(10) Patent No.: US 7,385,029 B2
(45) Date of Patent: Jun. 10, 2008

(54) METHOD OF MAKING TETRAPEPTIDE DERIVATIVE TZT-1027 CRYSTAL

(75) Inventors: Koichi Miyazaki, Ebina (JP); Katsuyuki Keino, Yokohama (JP); Arihiro Kanada, Kawasaki (JP); Nobuyoshi Minami, Yokohama (JP)

(73) Assignee: Teikoku Hormone Mfg. Co., Ltd., Tokyo (JP)

( * ) Notice: Subject to any disclaimer, the term of this patent is extended or adjusted under 35 U.S.C. 154(b) by 378 days.

(21) Appl. No.: 11/180,582

(22) Filed: Jul. 14, 2005

(65) Prior Publication Data

US 2005/0267041 A1 Dec. 1, 2005

Related U.S. Application Data

(62) Division of application No. 10/490,340, filed as application No. PCT/JP02/09628 on Sep. 19, 2002, now Pat. No. 7,008,928.

(30) Foreign Application Priority Data

Sep. 20, 2001 (JP) ............................. 2001-286674

(51) Int. Cl.
  *C07K 1/14* (2006.01)
  *C07K 5/10* (2006.01)
  *C07K 5/02* (2006.01)
  *C07K 1/00* (2006.01)
  *A61K 38/07* (2006.01)

(52) U.S. Cl. .................. 530/344; 530/330; 530/332; 530/333; 514/18

(58) Field of Classification Search ................ None
See application file for complete search history.

(56) References Cited

U.S. PATENT DOCUMENTS 4,978,744 A * 12/1990 Pettit et al. ............... 530/330

FOREIGN PATENT DOCUMENTS

| EP | 0 598 129 | 5/1994 |
|----|-----------|--------|
| EP | 0 600 745 | 6/1994 |
| JP | 07-002894 | 1/1995 |
| WO | 93/03054  | 2/1993 |

OTHER PUBLICATIONS

A. McPherson. Eur. J. Biochem (1990) 189, pp. 1-23.*
G.R. Pettit et al. J. Org. Chem. (1994) 59(11), pp. 2935-2938.*
J. Poncet et al. J. Med. Chem. (1998) 41(9), pp. 1524-1530.*
website: http://bcbsnj.myhealthyhorizon.com/topic/cancerdrugs.
website: http://web.archive.org/web/20010222115331/http://www.chem.vt.edu/chem-ed/diffraction/powder.html.
G. R. Pettit et al., "The Dolastatins. 21. Synthesis, X-ray Crystal Structure, and Molecular Modeling of (6R)-isodolastatin 10", The Journal of Organic Chemistry, vol. 59, No. 21, pp. 6127-6130, Oct. 21, 1994.
R. Giege et al., "Crystallogenesis of biological macromolecules: facts and perspectives", Acta. Crystallogr. D. Biol. Crystallogr., vol. 50 (P+4), pp. 339-350, Jul. 1994.
J. Poncet, "The Dolastatins, A Family of Promising Antineoplastic Agents", Current Pharmaceutical Design, No. 5, No. 3, pp. 139-162, 1999.
K. Miyazaki et al., "Synthesis and Antitumor Activity of Novel Dolastatin 10 Analogs", Chem. Phar. Bull., vol. 43, No. 10, pp. 1706-1718, 1995.

* cited by examiner

*Primary Examiner*—Andrew D Kosar
(74) *Attorney, Agent, or Firm*—Wenderoth, Lind & Ponack, L.L.P.

(57) ABSTRACT

The invention provides crystals of $N^2$-(N,N-dimethyl-L-valyl)-N-[(1S,2R)-2-methoxy-4-[(2S)-2-[(1R,2R)-1-methoxy-2-methyl-3-oxo-3-[(2-phenylethyl)amino]propyl]-1-pyrrolidinyl]-1-[(S)-1-methylpropyl]-4-oxobutyl]-N-methyl-L-valinamide or salts thereof which possess potent antitumor activity and methods for their preparation.

6 Claims, 2 Drawing Sheets

METHOD OF MAKING TETRAPEPTIDE DERIVATIVE TZT-1027 CRYSTAL

This application is a divisional of Ser. No. 10/490,340 filed Mar. 22, 2004 now U.S. Pat. No. 7,008,928, which is a U.S. national stage of International Application No. PCT/JP02/09628 filed Sep. 19, 2002.

TECHNICAL FIELD

This invention relates to the novel crystals of tetrapeptide derivative which are useful as an active ingredient in pharmaceutical preparations, and a process for their preparation.

BACKGROUND ART $N^2$-(N,N-dimethyl-L-valyl)-N-[(1S,2R)-2-methoxy-4-[(2S)-2-[(1R,2R)-1-methoxy-2-methyl-3-oxo-3-[(2-phenylethyl)amino]propyl]-1-pyrrolidinyl]-1-[(S)-1-methylpropyl]-4-oxobutyl]-N-methyl-L-valinamide [TZT-1027] represented by the following formula (I)

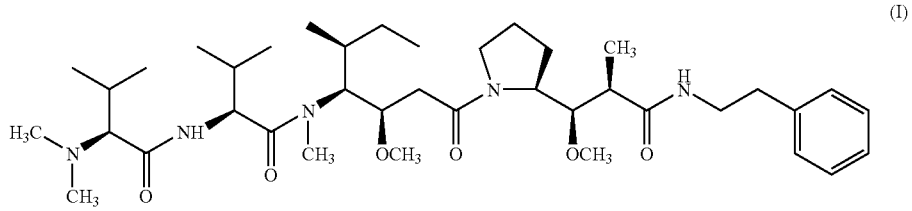

(I)

is a tetrapeptide derivative possessing potent antitumor activity, and is a potential anti-cancer agent.

TZT-1027 per se has been disclosed in, for example, PCT International Publication WO93/03054 Pamphlet, which describes purification of crude TZT-1027 with preparative thin-layer chromatography and column chromatography, to provide amorphous TZT-1027 powder. Chem. Pharm. Bull., 43(10), 1706-1718 (1995) also describes purification of crude product first by means of flash chromatography or preparative thin-layer chromatography and then column chromatography to provide TZT-1027 as an amorphous powder. JP Hei 7 (1995)-2894A, furthermore, discloses TZT-1027, in which again crude TZT-1027 was purified by column chromatography and preparative thin-layer chromatography to provide a fluffy solid TZT-1027.

As above, amorphous TZT-1027 has been reported in the past, but no literature disclosing crystalline TZT-1027 is found.

Generally speaking, compounds in amorphous form require more complicated purification operations than those in crystalline form do, and frequently their stability is insufficient. In particular, where the compounds are used as active ingredients of pharmaceutical compositions, their insufficient purity can provide problems. In also formulation operations, where the compounds are in amorphous form, amorphous powder is apt to be blown up and require more cautious handling than cases of formulating crystalline compounds. For these reasons, in using TZT-1027 having potent antitumor activity as an active ingredient of pharmaceutical compositions, crystalline TZT-1027 is considered preferable compared to known amorphous form.

We have made various attempts to crystallize TZT-1027, but its crystallization was very difficult because it is a peptide compound. For instance, TZT-1027 crystals could not be obtained through crystallization using such solvents as alcohols, halogenated hydrocarbons, nitrites, ketones, organic acids, water and the like. We furthermore tried the crystallization using ethers such as diisopropyl ether, tetrahydrofuran and the like, or hydrocarbons such as n-pentane, n-hexane, cyclohexane and the like without success.

BRIEF SUMMARY OF THE INVENTION

We now discovered, surprisingly, that crystals of TZT-1027 or salts thereof could be easily obtained by treating crude TZT-1027 or salts thereof with a single solvent of diethyl ether or ethyl acetate, or a mixed solvent formed of esters and hydrocarbons and/or ethers, and have succeeded for the first time in the world to provide TZT-1027 or salts thereof as crystals.

Thus, the present invention provides crystals of TZT-1027 or salts thereof.

According to the invention, TZT-1027 or salts thereof of at least 99% in purity, i.e., at a purity level sufficient for pharmaceuticals, through simple and convenient purification means such as crystallization or recrystallization, and furthermore so obtained crystalline TZT-1027 or salts thereof show little quality unevenness and excel in stability compared with amorphous ones.

DETAILED DESCRIPTION OF THE INVENTION

Figure 1:
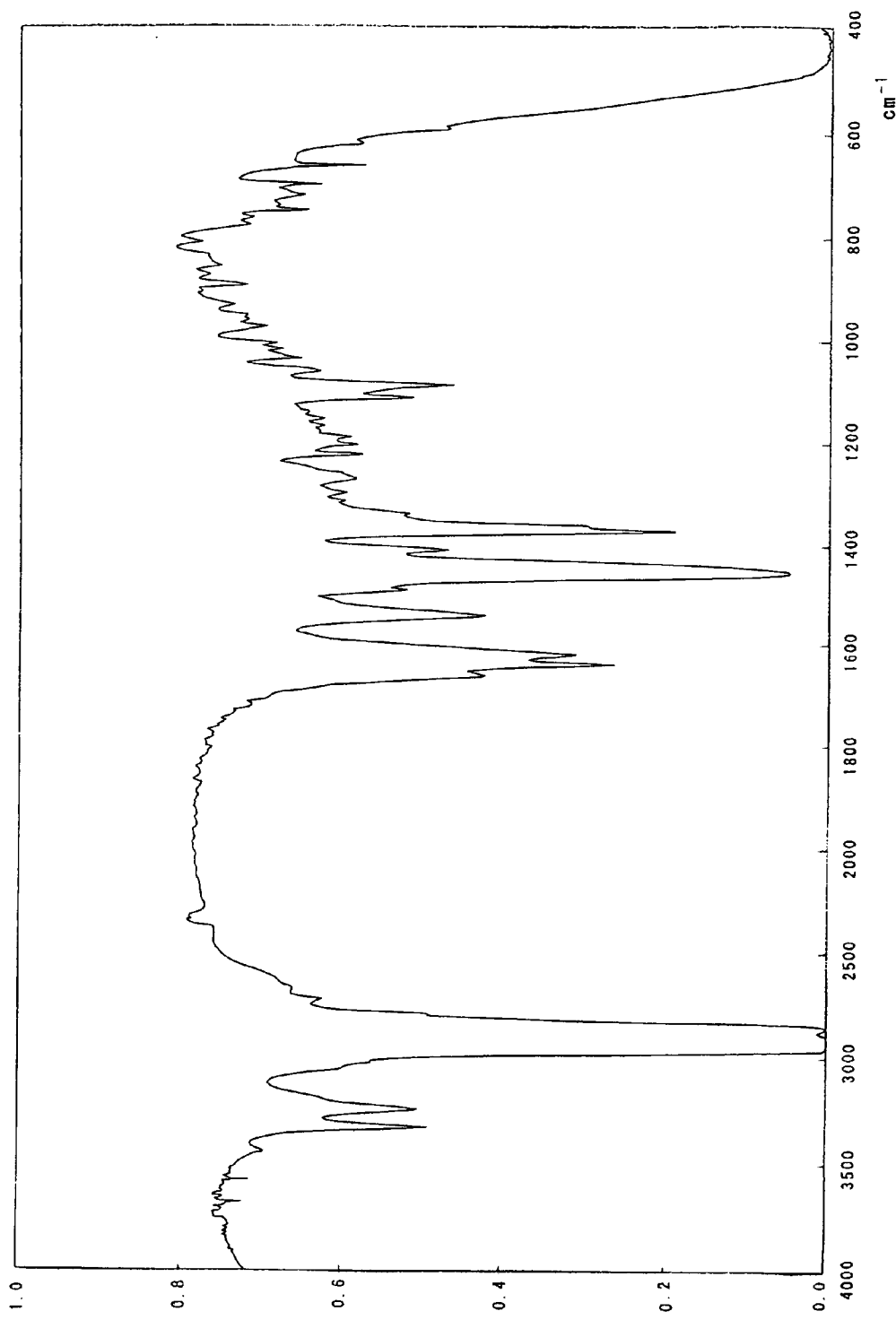
FIG. 1 is an IR spectrum of TZT-1027 crystal.
Figure 2:
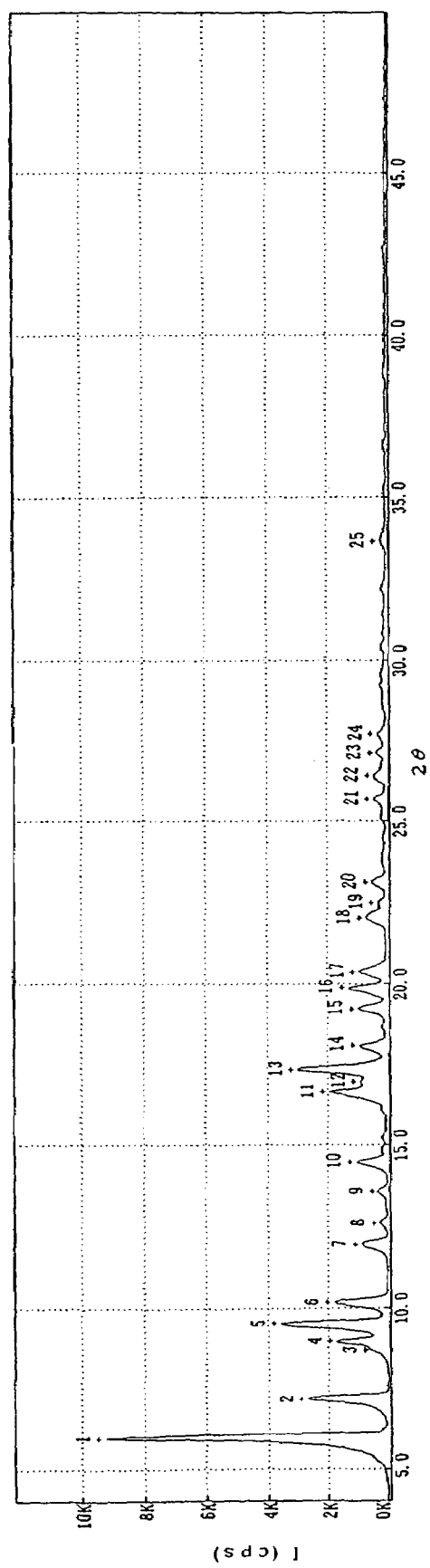
FIG. 2 shows a powder X-ray diffraction pattern of TZT-1027 crystal.

TZT-1027 possesses potent antitumor activity and has very strong toxicity also to normal cells. Scrupulous care is therefore required for its purification operations and formulation operations into pharmaceutical preparations. For example, an operator's health may be endangered when he is exposed to TZT-1027 even for a short time or to a minor extent, and sufficient caution is essential for its handling. In the purification procedures by conventional chromatographic means or formulation procedures using the amorphous bulk, the operator's risk for being exposed to TZT-1027 dust is very high. Whereas, purification procedures of crystalline TZT-1027 provided by the present invention is simpler compared with that of amorphous TZT-1027 and causes little scattering of dust. Formulation operations also are easier and handlability of TZT-1027 is drastically improved.

From the result of analyzing the crystalline structure using X-rays, the crystal system of TZT-1027 according to the present invention is found to be orthorhombic and to have the lattice parameters of a=18.180 Å, b=24.419 Å and c=10.632 Å. Also in the powder X-ray diffraction pattern, TZT-1027 crystal provided by the present invention has characteristic peaks at interplanar spacing (d) of 14.72, 12.27, 9.84, 9.28, 8.68, 7.39, 6.11, 5.32, 5.10, 4.90, 4.61, 4.47 and 4.36 Å. Here the term "characteristic peaks" is used in the sense that they are "relatively intense peaks" in the powder x-ray diffraction pattern, and in Table 1 appearing later in this specification, the peaks having $I/I_0$ values of 90 or higher are called "characteristic peaks".

TZT-1027 can be crystallized in the form of a free base or, where necessary, first converted to pharmaceutically acceptable salts with inorganic or organic acids and then crystallized. As examples of inorganic acid useful for forming the salt, hydrochloric acid, hydrobromic acid, nitric acid, sulfuric acid and phosphoric acid can be named, and as examples of useful organic acid, acetic acid, propionic acid, maleic acid, fumaric acid, malonic acid, succinic acid, lactic acid, malic acid, tartaric acid, citric acid, benzoic acid and methanesulfonic acid can be named.

As stated above, we have for the first time succeeded in obtaining TZT-1027 crystal, using as the crystallization solvent a single solvent system of diethyl ether or ethyl acetate or a mixed solvent system of esters and hydrocarbons and/or ethers. Whereas, TZT-1027 crystal is obtainable not only by crystallization from such solutions but also by such a method as crystallization from a melt.

In the present specification, "crystallization" signifies an operation to convert a compound in any form other than crystal into crystalline compound, and "recrystallization" signifies an operation to make a crystalline compound to a compound of more purified crystalline form.

As crystallization methods from solutions, for example, concentration, gradual cooling, reaction (diffusion, electrolysis), hydrothermal growing and flux methods can be named. As the solvent which can be used in those crystallization methods, where a single solvent is used, diethyl ether or ethyl acetate can be named; and where mixed solvent is used, those composed of combinations of esters and hydrocarbons and/or ethers can be named. Examples of ester herein are ethyl acetate, methyl acetate and the like; examples of hydrocarbon are n-hexane, n-heptane, cyclohexane, toluene, xylene and the like; and examples of ether are diethyl ether, diisopropyl ether, tetrahydrofuran, dioxane and the like. Of these, particularly such combinations as ethyl acetate/n-pentane, ethyl acetate/n-hexane and ethyl acetate/diethyl ether are suitable as the mixed solvent. Where solvents are used in combination, the use ratio is not subject to particular limitations, while generally adequate use ratios in esters/hydrocarbons or ethers are within a range of from 1/1 to 1/10.

In the crystallization from solutions as above, the crystallization can be effected by first dissolving amorphous TZT-1027 in a solvent as above-described, e.g., diethyl ether, under heating at around 40° C., and then cooling the solution, or first concentrating and then cooling. The TZT-1027 concentration in the solution is preferably around 15-30 wt %, and cooling to from about 0° to about 25° C. is preferred. When a mixed solvent is used, the crystallization can be effected by, for example, dissolving amorphous TZT-1027 in an ester solvent such as ethyl acetate at temperatures around 40-77° C., and then adding to the resultant solution about 0.5-5 volume times the ester solvent of a hydrocarbon solvent such as n-pentane, n-hexane or the like. Here the concentration of the amorphous TZT-1027 in the ester solvent solution is preferably about 10-40 wt %. At the time of adding the hydrocarbon solvent, preferably the liquid temperature is cooled to about 0-30° C. Under such preferred conditions, crystallization of TZT-1027 can be carried out with industrial advantage.

Also as crystallization methods from melts, for example, normal freezing method (pull method, temperature gradient method, Bridgman's method), zone melting methods (zone leveling method, float zone method), and special growth method (VLS method, liquid phase epitaxy method) can be named.

Thus obtained crystals can be recrystallized, where their purity is insufficient. Recrystallization can be carried out by repeating any of above-described crystallization methods or by suitably combining those crystallization methods.

Thus obtained TZT-1027 crystals might contain, particularly when they are crystallized from solutions, molecules of the solvent which is used for the crystallization or recrystallization therein. In such a case, the solvent molecules in the crystals must be removed before the crystals of the present invention are used as the active ingredient of pharmaceutical compositions. Removal of the solvent can be done by, for example, pulverizing the crystals and drying the powders under reduced pressure. Accordingly, TZT-1027 crystals of the present invention include, besides those referred to as single crystal, those in a form of crystalline powder which is advantageously used as an active ingredient of pharmaceutical compositions.

Where crystals of TZT-1027 or salts thereof are used as an active ingredient of pharmaceutical compositions, they can be formulated into preparation forms such as solid forms (e.g., tablets, hard capsules, soft capsules, granules, powders, fine granules, pills or troches); semi-solid forms (e.g., suppositories or ointments); or liquid forms (e.g., injections, emulsions, suspensions, elixiers, lotions or sprays), together with pharmaceutically acceptable adjuvants for drug. As useful adjuvants in manufacturing such preparations, for example, starch, glucose, sucrose, lactose, fructose, maltose, mannitol, sorbitol, cyclodextrin, silicic acid derivatives, methyl cellulose, carboxymethyl cellulose or salts thereof, alginate, gelatine, polyvinylpyrrolidone, calcium carbonate, sodium hydrogencarbonate, magnesium carbonate, talc, magnesium stearate, gum arabic, polyethylene glycol, p-hydroxybenzoic acid alkyl ester, cetyl alcohol, syrup, ethanol, propylene glycol, vaseline, carbowax, glycerine, sodium chloride, sodium sulfite, sodium phosphate, citric acid, lactic acid, polylactic acid and polylactic acid-glycolic acid can be named.

While the content of TZT-1027 or a salt(s) thereof in such preparations is variable depending on individual preparation forms, it is generally desirable to use TZT-1027 or salt(s) thereof at a concentration level within a range of 0.1-50 wt % for solid and semi-solid preparation forms; and at a concentration level within a range of 0.05-10 wt % for liquid preparation forms.

According to the present invention, where crystals of TZT-1027 or salt(s) thereof are used as the active ingredient of anti-tumor agents, it is particularly preferred to use them as formulated into injections or orally administerable preparations.

EXAMPLES

Hereinafter the present invention is more specifically explained, referring to working examples.

In the following examples, melting points were measured with Yamato Melting Point Apparatus (MP-21 Model). Infrared absorption spectra were measured by the paste method according to Japanese pharmacopeia, general test method, with Perkin- Elmer FT-IR Spectrometer (1600 Series). Ultraviolet absorption spectra were measured with Hitachi U-3210 Spectrophotometer, as to 0.01 mol/L hydrochloric acid-ethanol (95%) solution of TZT-1027, by the absorptiometric method according to Japanese pharmacopeia, general testing method. Nuclear magnetic resonance spectra were measured in deuterated chloroform with JEOL JNM-LA500 FT-NMR Spectrometer, using tetramethylsilane (TMS) as the internal standard substance. Powder X-ray diffraction was measured with MAC Science Powder X-ray Diffraction System (MXP[3]). Optical rotation was measured with JASCO DIP-140 Digital Polarimeter, as to TZT-1027's ethanol (95%) solution at a layer length of 100 mm, using sodium D ray. X-ray diffraction data of the crystals were measured with a tetraxial diffractiometer (RIGAKU AFC7R) using Cu-Kα ray, determining the initial phase by the direct method, and the structure was made precise with SHELXL-93.

Example 1

Preparation of $N^2$-(N,N-dimethyl-L-valyl)-N-[(1S,2R)-2-methoxy-4-[(2S)-2-[(1R,2R)-1-methoxy-2-methyl-3-oxo-3-[(2-phenylethyl)amino]propyl]-1-pyrrolidinyl]-1-[(S)-1-methylpropyl]-4-oxobutyl]-N-methyl-L-valinamide [TZT-1027] crystal:

Following the method as described at page 1718, left col., lines 20-26 of Chem. Pharm. Bull., 43(10), 1706-1718, (1995), Dov-Val-Dil-Dap-OBzl was debenzylated in t-butanol/water (9:1) in hydrogen atmosphere in the presence of 5% palladium-on-carbon catalyst, and then reacted with β-phenethylamine in dimethylformamide in the presence of diethyl cyanophosphate and triethylamine. So obtained 5.0 g of crude TZT-1027 was dissolve in 20 ml of dry diethyl ether and stirred for about 3 hours at room temperature. Whereupon precipitated crude crystal was recovered by filtration, to which 25 ml of ethyl acetate was added. Completely dissolving the crude crystal in the ethyl acetate at about 40-60° C., the solution was heated and concentrated on an oil bath of about 110° C. until the distilled amount of ethyl acetate reached about 15 ml. So concentrated solution was gradually cooled in a water bath under stirring, to about 30° C. Then, while continuing the gradual cooling until the bath temperature dropped to 10° C., 20 ml of n-pentane was dripped into the solution in three divided times, followed by further 30 minutes' stirring at the bath temperature of 10° C. and standing at room temperature for 30 minutes. The crystal whereby precipitated was recovered by filtration, washed twice with 9 ml of n-pentane/ethyl acetate (2:1) liquid mixture, and dried under reduced pressure to provide 4.8 g of TZT-1027 crystal (HPLC purity: 99.3%).

Melting point: 85-90° C.

$^1$H-NMR, 500 MHz (CDCl$_3$, δ): 0.81 (3H, t, J=7.5 Hz), 0.90-1.09 (3H×5, m), 1.21 (3H, d, J=7.0 Hz), 1.67-1.78 (2H, m), 1.89-1.95 (2H, m), 1.99 (1H, sextet, J=6.6 Hz), 2.07 (1H, sextet, J=6.7 Hz), 2.24 (3H×2, s), 2.35-2.40 (2H, m), 2.43 (1H, d, J=6.4 Hz), 2.83 (2H, t, J=7.0 Hz), 3.01 (3H, s), 3.30 (3H, s), 3.35 (3H, s), 3.41-3.57 (2H, m), 3.84 (1H, dd, J=8.1 Hz, J=2.3 Hz), 4.05-4.08 (1H, m), 4.12 (1H, broad ddd), 4.77 (1H, dd, J=9.2 Hz, J=6.7 Hz), 6.48 (1H, broad t), 6.87 (1H, d, J=9.2 Hz), 7.16-7.31 (5H, m)

IR(ν, nujol): 3330, 3250, 1640, 1621, 1090 cm$^{-1}$

The product's IR spectrum is shown as FIG. 1.

UVmax(HCl—C$_2$H$_5$OH): absorption maxima at 252.8 nm, 258.5 nm, 267.7 nm $[\alpha]_D^{20}$: −38.4° [c=0.5, ethanol (95)]

The powder X-ray diffraction data are shown in Table 1.

TABLE 1

| No. | 2Theta | d | I(cps) | I/Io | FWHM |
|---|---|---|---|---|---|
| 1: | 6.0000 | 14.7167 | 9289 | 1000 | 0.1600 |
| 2: | 7.2000 | 12.2670 | 2677 | 281 | 0.1800 |
| 3: | 8.6800 | 10.1782 | 621 | 55 | 0.0600 |
| 4: | 8.9800 | 9.8387 | 1726 | 175 | 0.1600 |
| 5: | 9.5200 | 9.2825 | 3601 | 379 | 0.2000 |
| 6: | 10.1800 | 8.6821 | 1823 | 186 | 0.2200 |
| 7: | 11.9600 | 7.3932 | 938 | 91 | 0.2400 |
| 8: | 12.6200 | 7.0083 | 337 | 24 | 0.2000 |
| 9: | 13.5800 | 6.5147 | 386 | 28 | 0.2200 |
| 10: | 14.4800 | 6.1118 | 1102 | 106 | 0.2200 |
| 11: | 16.6600 | 5.3167 | 1949 | 190 | 0.2200 |
| 12: | 16.9600 | 5.2233 | 966 | 82 | 0.0600 |
| 13: | 17.3600 | 5.1039 | 3010 | 306 | 0.2000 |
| 14: | 18.0800 | 4.9023 | 1006 | 90 | 0.2200 |
| 15: | 19.2200 | 4.6139 | 1027 | 92 | 0.2400 |
| 16: | 19.8600 | 4.4667 | 1332 | 126 | 0.2000 |
| 17: | 20.3600 | 4.3581 | 992 | 90 | 0.2400 |
| 18: | 22.0000 | 4.0369 | 776 | 68 | 0.3400 |
| 19: | 22.4800 | 3.9517 | 396 | 25 | 0.1600 |
| 20: | 23.1200 | 3.8437 | 588 | 45 | 0.2400 |
| 21: | 25.7000 | 3.4634 | 507 | 36 | 0.2000 |
| 22: | 26.4400 | 3.3682 | 523 | 37 | 0.3000 |
| 23: | 27.1600 | 3.2805 | 434 | 28 | 0.2000 |
| 24: | 27.7600 | 3.2109 | 391 | 24 | 0.2400 |
| 25: | 33.6800 | 2.6589 | 303 | 20 | 0.3000 |

Example 2

Following the method as described in Example 28 of PCT International Publication WO93/03054 pamphlet, a compound obtained by deprotecting t-butyl(3R,4S,5S)-4-[N-[(N,N-dimethyl-L-valyl)-L-valyl]-N-methylamino]-3-methoxy-5-methylheptanoate (Dov-Val-Dil-Obu$^r$) in dichloromethane with trifluoroacetic acid and a compound obtained by deprotecting (2S)-2-[(1'R,2'R)-1-methoxy-2-methyl-3-oxo-3-[(2-phenylethyl)amino]propyl]-1-(t-butyloxycarbonylpyrrolidine) (Boc-Dap-NHCH$_2$CH$_2$-Ph) with hydrogen chloride/ethyl acetate were condensed in dimethylformamide, in the presence of diethyl cyanophosphate and triethylamine. So obtained 11.1 g of crude product was dissolved in 48 ml of dry diethyl ether and stirred for about 3 hours at room temperature. Whereby precipitated crude crystal was recovered by filtration, to which 20 ml of ethyl acetate was added to completely dissolve the crude crystal therein at about 50° C. The solution was gradually cooled in a water bath to about 30° C. under stirring, and while further continuing the gradual cooling until the bath temperature reached 10° C., 60 ml of diethyl ether was dripped thereinto in three divided times. After the dripping, stirring was continued for further 30 minutes at the bath temperature of 10° C., followed by 30 minutes' standing at room temperature. The precipitated crystal was recovered by filtration, washed twice with 20 ml of diethyl ether/ethyl acetate (3:1) liquid mixture, and dried under reduced pressure to provide 8.42 g of TZT-1027 crystal (HPLC purity: 99.2%).

Example 3

Preparation of a crystal for analyzing the single crystal structure:

Two (2.0) mg of crystalline powder of the TZT-1027 which was obtained in Example 1 was dissolved in 0.5 ml of ethyl acetate, and 0.5 ml of n-pentane was added to the formed solution. The sample tube containing this solution was put in a vessel containing 5 ml of n-pentane and sealed hermetically. Allowing the sealed vessel to stand in a refrigerator maintained at about 0° C. for 5 days, a crystal suitable for analyzing the single crystal structure was obtained.

The crystalline data obtained by the structural analysis of the single crystal are as shown in the following Table 2.

TABLE 2

| | |
|---|---|
| Compositional formula: | C$_{39}$H$_{67}$N$_5$O$_6$ |
| Molecular weight: | 701.98 |
| Crystal color: | colorless |
| Crystal configuration: | prismatic |
| Crystal system: | orthorhombic system |
| Space group: | P2$_1$2$_1$2$_1$ |
| Lattice constants: | a = 18.180Å |
| | b = 24.419Å |
| | c = 10.632Å |
| Unit lattice volume: | V = 4719Å$^3$ |
| Number of molecules in unit lattice: | Z = 4 |
| Crystal density (calculated): | Dcalc = 1.089 g/cm$^3$ |
| R factor: | R(F) = 0.050 (I > 2σ(I)) |

The invention claimed is:

1. A method of making crystals of N$^2$-(N,N-dimethyl-L-valyl)-N-[(1 S,2R)-2-methoxy-4-[(2S)-2-[(1R,2R)-1-methoxy-2-methyl-3-oxo-3-[(2-phenylethyl)amino]propyl]-1-pyrrolidinyl]-1-[(S)-1-methylpropyl]-4-oxobutyl]-N-methyl-L-valinamide (TZT-1027) represented by the following formula (I) or a salt thereof:

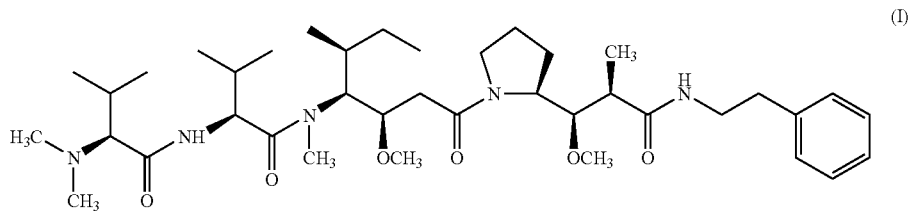

(I)

which comprises crystallizing amorphous TZT-1027 or a salt thereof from diethyl ether; and optionally recrystallizing the formed crystals.

2. The method according to claim 1, in which the recrystallization is performed from a mixed solvent selected from combinations of esters and hydrocarbons and/or ethers.

3. The method according to claim 2, in which the ester is selected from the group consisting of ethyl acetate and methyl acetate; the hydrocarbon is selected from the group consisting of n-pentane, n-hexane, n-heptane, cyclohexane, toluene and xylene; and the ether is selected from the group consisting of diethyl ether, diisopropyl ether, tetrahydrofuran and dioxane.

4. The method according to claim 2, in which the ratio of ester/hydrocarbon or ether is within a range of from 1/1 to 1/10.

5. The method according to claim 2, in which the ester is ethyl acetate; the hydrocarbon is n-pentane or n-hexane; and the ether is diethyl ether.

6. The method according to claim 2, which comprises dissolving TZT-1027 crystals in an ester solvent at a temperature around 40-77° C., and then adding to the resultant solution a hydrocarbon or ether solvent in about 0.5-5 volume times the amount of the ester solvent, optionally after cooling the solution to a liquid temperature of about 0-30° C.

* * * * *